United States Patent [19]

Rossignol

[11] Patent Number: 4,818,767

[45] Date of Patent: Apr. 4, 1989

[54] QUINATE SALTS OF ANTIMALARIAL PHENANTHRENEMETHANOL COMPOUNDS

[75] Inventor: Jean F. Rossignol, Philadelphia, Pa.

[73] Assignee: SmithKline Beckman Corporation, Philadelphia, Pa.

[21] Appl. No.: 548,181

[22] Filed: Nov. 2, 1983

[51] Int. Cl.⁴ .......................................... A61K 31/205
[52] U.S. Cl. ................................ 514/555; 260/501.18; 514/653; 514/895; 564/355
[58] Field of Search ................ 564/355; 424/316, 330; 260/501.18; 514/684

[56] References Cited

U.S. PATENT DOCUMENTS 3,097,243  7/1963  Cutler ......................... 260/501.18 X
4,178,376 12/1979  Higuchi et al. ...................... 424/258

OTHER PUBLICATIONS

Am. J. Trop. Med. Hyg., 31(6), 1982, pp. 1075–1079.
Am. J. Trop. Med. Hyg., 25(6), 1976, pp. 769–774.
J. Med. Chem., 15(7), 1972, pp. 771–775.
Annals Trop Med. Para., 73(6), 1979, pp. 505–525.

Primary Examiner—Robert V. Hines
Attorney, Agent, or Firm—Stuart R. Suter; Alan D. Lourie; Janice E. Williams

[57] ABSTRACT

The compounds of formula (I)

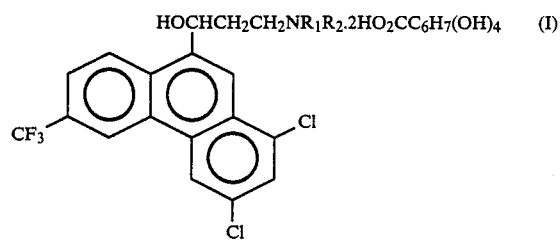

$$HOCHCH_2CH_2NR_1R_2 \cdot 2HO_2CC_6H_7(OH)_4 \quad (I)$$

wherein $R_1$ is hydrogen or an alkyl radical containing one to six carbon atoms and $R_2$ is an alkyl radical containing one to six carbon atoms possess markedly increased activity against malaria-causing parasites. Pharmaceutical compositions and method of treatment of subjects with malaria are also disclosed.

7 Claims, No Drawings

QUINATE SALTS OF ANTIMALARIAL PHENANTHRENEMETHANOL COMPOUNDS

This invention was made under an Agreement with the Department of the Army and the government has certain rights in this invention.

BACKGROUND OF THE INVENTION

A number of phenanthrenemethanol compounds have been shown to exhibit antimalarial activity in humans against both chloroquine-sensitive and resistant strains of *Plasmodium falciparum*. The evaluation of the antimalarial activity of the phenanthrenemethanol, halofantrine or 1-[1,3-dichloro-6-trifluoromethyl-9-phenanthryl]-3-di-(n-butyl)-aminopropanol hydrochloride, was reported in the American Journal of Tropical Medicine and Hygiene, Vol. 31 (6) pages 1075–79 (1982). Halofantrine was effective when administered over a short period of time and with a minimum of two doses against the multi-drug resistant Vietnam Smith strain and Cambodian Buchanan strain of *P. falciparum* and the Chesson strain of *P. vivax*. However, problems with systemic bioavailability remained. A means for enhancing the bioavailability of a number of phenanthrenemethanol antimalarial compounds, including halofantrine, utilizing specific organic fatty acids, as adjuvants, has been disclosed in U.S. Pat. No. 4,178,376.

SUMMARY OF THE INVENTION

This invention relates to the quinate salts of the class of antimalarial compounds containing halofantrine (as the free base) and its analogs. These salts exhibit markedly increased activity against malaria-causing parasites when compared to the hydrochloride salts reported in the literature. Pharmaceutical compositions and methods of treatment of subjects with malaria are also disclosed.

DETAILED DESCRIPTION OF THE INVENTION

The compounds represented by the following structural formula (I):

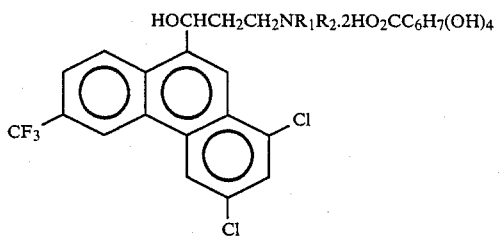

$$HOCHCH_2CH_2NR_1R_2 \cdot 2HO_2CC_6H_7(OH)_4 \quad (I)$$

wherein $R_1$ is hydrogen or an alkyl radical containing one to six carbon atoms and $R_2$ is an alkyl radical containing one to six carbon atoms, possess markedly increased activity against malaria-causing parasites.

A particular class of compounds of this invention are those compounds of formula (I) wherein $R_1$ is an alkyl radical containing one to six carbon atoms. Exemplifying this class of compounds is 1-[1,3-dichloro-6-trifluoromethyl-9-phenanthryl]-3-di(n-butyl)aminopropanol quinate, a compound of formula (I) wherein both $R_1$ and $R_2$ are n-butyl radicals.

A second class of compounds of this invention are those compounds of the formula (I) wherein $R_1$ is hydrogen. Exemplifying the class of compounds is 1-[1,3-dichloro-6-trifluoromethyl-9-phenanthryl]-3-n-butylaminopropanol quinate, a compound of formula (I) wherein $R_1$ is hydrogen and $R_2$ is a n-butyl radical.

The compounds of this invention are conveniently prepared by reacting quinic acid (1,3,4,5-tetrahydroxycyclohexanecarboxylic acid) with a compound of the formula (II):

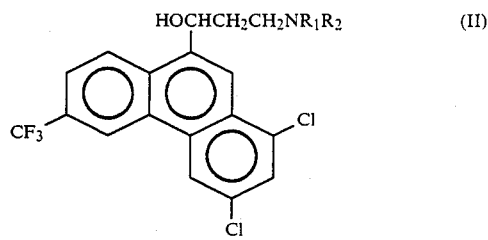

$$HOCHCH_2CH_2NR_1R_2 \quad (II)$$

wherein $R_1$ and $R_2$ are described above in an inert solvent. The amount of quinic acid employed in this reaction can be between 1.50 and 2.50 moles per mole of the compound of the formula (II) but 2.0 moles of quinic acid is preferred. The compound of formula (II) is mixed with the appropriate amount of quinic acid (50% aqueous solution) and the inert solvent is added to affect solution of the reactants at a temperature selected from the range of ambient temperature to 100° C. The reaction solution is filtered and the filtrate is heated under reduced pressure up to 100° C. to remove the solvent. Upon concentration to dryness, the compounds of the formula (I) solidify and are collected and dried. The compounds of the formula (I) are partially water soluble to about 20 percent on a weight by weight basis.

Examples of the inert solvents which are utilized in the process are alcohols, such as, methanol, ethanol, isopropanol and the like and amides, such as dimethylformamide and dimethylacetamide.

The bases of the formula (II) are prepared according to the general procedures described in the Journal of Medicinal Chemistry, Vol 15, No. 7, pages 771–5 (1972) wherein the process for converting substituted phenanthrene-9-carboxylic acid into the desired compounds as the free base form are detailed.

The antimalarial activities of the compounds of this invention is demonstrated in a standard pharmacological in vivo test procedure against *P. berghei* in Swiss mice.

The antimalarial activity of 1-[1,3-dichloro-6-trifluoromethyl-9-phenanthryl]-3-di(n-butyl)aminopropanol quinate (Compound A) was established utilizing the following methodology. Test animals were infected by interperitoneal injection of $9 \times 10^6$ parasitized cells of *P. berghei* contained in 0.25 ml of 1:40 dilution in 0.9% aqueous sodium chloride with potassium citrate added of donor mouse blood which was infected with *P. berghei* one week earlier. Three days after injection, 3 groups of 4 mice (2 males and 2 females) were treated with Compound A at a dose level of 1, 4 and 16 mg/kg/day for 4 consecutive days. Similarly, a positive control of 3 groups of 4 mice (2 males and 2 females) were treated with halofantrine, as the hydrochloride salt, at a dose level of 1, 4 and 16 mg/kg/day for 4 consecutive days. The route of administration of Compound A and halofantrine was oral intubation of a suspension of each compound in 0.2% methyl cellulose at a constant volume of 20 ml. A negative control group of 4 mice (2 males and 2 females) remained untreated. The results of the above test procedure expressed as an ED$_{50}$ (the effective dose which decrease the cell parasitemia by 50 percent on day 4 of treatment) are shown below in Table I.

TABLE I

| Dose<br>mg/kg/day × 4 days | Number of Animals | ED$_{50}$ Day 4<br>(mean values) |
|---|---|---|
| Halofantrine (HCl) | | |
| 1 mg/kg/day | 4 | 6 mg/kg |
| 4 mg/kg/day | 4 | |
| 16 mg/kg/day | 4 | |
| Compound A | | |
| 1 mg/kg/day | 4 | ≦1 mg/kg |
| 4 mg/kg/day | 4 | |
| 16 mg/kg/day | 4 | |

Compound A is at least 6 times more effective, on a weight by weight basis, in the treatment of P. berghei malaria in mice using as an efficacy criterion the ED$_{50}$ calculation of deparasited cells on day 4 when compared to halofantrine hydrochloride. [See Annals of Tropical Medicine and Parasitology, 73, pp 505–525, (1979)]

The pharmaceutical compositions of this invention containing a compound of formula (I) which has antimalarial activity are prepared in conventional dosage unit forms by incorporating the chemical compound with a nontoxic pharmaceutical carrier according to accepted procedures. A nontoxic quantity of said active ingredient is chosen which is sufficient to produce the desired chemotherapeutic activity in a subject, animal or human, without unacceptable toxicity. The compositions will contain the active ingredient in such an effective but nontoxic amount selected from about 125 mg to about 1000 mg of active ingredient per dosage unit but this quantity depends on the specific biological activity desired, the activity of the compound and the conditions of the patient.

A wide variety of pharmaceutical forms can be employed. Thus, if a solid carrier for oral administration is used the preparation can be tableted, placed in a hard gelatin capsule in powder or pellet form, or in the form of a suppository, trouche or lozenge. The amount of solid carrier will vary widely but preferably will be from about 125 mg to about 500 mg. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional technique of the pharmaceutical chemist involving mixing, granulating and compressing when necessary, or variously mixing and dissolving the ingredients as appropriate to give the desired end product.

The method of producing antimalarial activity, curatively or prophylactically, comprises administering internally to a subject in need of such activity a compound of formula (I), usually combined with a pharmaceutical carrier, in a nontoxic amount sufficient to produce said activity as described above. The route of administration may be any route which effectively transports the active compound to the site of action which is to be affected within the body such as orally or parenterally. Advantageously, a single oral dose or equal oral doses will be administered several times such as from 1–3 times a day with the daily dosage regimen being selected from about 125 mg to about 1000 mg.

The following examples illustrate the preparations of the compounds of formula (I) and their incorporation into pharmaceutical compositions and as such are not to be considered as limiting the invention set forth in the claims appended hereto.

EXAMPLE 1

Preparation of 1-[1,3-dichloro-6-trifluoromethyl-9-phenanthryl]-3-di(n-butyl)aminopropanol quinate (Compound A).

To a 50% aqueous solution of quinic acid (4.62 g) at ambient temperature with stirring was added 1-[1,3-dichloro-6-trifluoromethyl-9-phenanthryl]-3-di(n-butyl)aminopropanol (6 g). To the mixture was added ethanol (500 ml) and the mixture is heated to about 100° C. to affect solution. The solution is then filtered and the ethanol and water removed under vacuum until dryness. The desired product solidifies as a white crystalline material with a melting point of about 90° C. and is soluble in water up to 20 percent on a weight to weight basis. Elemental analysis is as follows: Calculated C, 54.29; H, 6.32; N, 1.58 and Cl, 8.03; F, 6.44. Found C, 54.32; H, 6.24; N, 1.66 and Cl, 7.95; F, 6.49.

Utilizing the general procedure of Example 1 the following compounds of formula (I) are prepared from quinic acid and the appropriate phenanthrenemethanol of formula (II):

| Compound | R$_1$ | R$_2$ |
|---|---|---|
| B | H | n-Butyl |
| C | H | i-Propyl |
| D | H | n-Hexyl |
| E | Ethyl | Ethyl |
| F | i-Propyl | i-Propyl |
| G | n-Hexyl | n-Hexyl |

EXAMPLE 2

As a specific embodiment of a composition of this invention, an active ingredient, such as one part of Compound A, is dissolved in 20 parts of 0.2 percent aqueous methyl cellulose and is administered orally in one dose of 4 mg/kg to a subject in need of treatment of malaria.

What is claimed is:

1. A compound represented by the following structural formula (I):

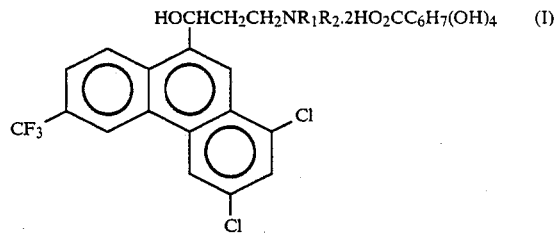

HOCHCH$_2$CH$_2$NR$_1$R$_2$·2HO$_2$CC$_6$H$_7$(OH)$_4$    (I)

wherein R$_1$ is hydrogen or an alkyl radical containing one to six carbon atoms and R$_2$ is an alkyl radical containing one to six carbon atoms.

2. A compound of claim 1 wherein R$_1$ is an alkyl radical containing one to six carbon atoms.

3. A compound of claim 2 wherein both R$_1$ and R$_2$ are n-butyl radicals, which is 1-[1,3-dichloro-6-trifluoromethyl-9-phenanthryl]-3-di(n-butyl)aminopropanol quinate.

4. A compound of claim 1 wherein $R_1$ is hydrogen.

5. A pharmaceutical composition for the treatment of malaria comprising a nontoxic antimalarial quantity of a compound of claim 1 and a pharmaceutically acceptable carrier therefor.

6. A composition of claim 5 in which the quantity of the compound is selected from the range of from 125 mg. to about 1000 mg.

7. A method for the treatment of malaria in a subject in need of said treatment comprising administering orally or by injection a nontoxic antimalarial quantity of a compound of claim 1.

* * * * *